United States Patent [19]
Carlson

[11] Patent Number: 5,547,909
[45] Date of Patent: Aug. 20, 1996

[54] REGENERATION OF HYDROGEN FLUORIDE ALKYLATION CATALYST

[75] Inventor: LeRoy W. Carlson, Bartlesville, Okla.

[73] Assignee: Phillips Petroleum Company, Bartlesville, Okla.

[21] Appl. No.: 200,978

[22] Filed: Feb. 24, 1994

[51] Int. Cl.$^6$ .................................. B01J 20/34
[52] U.S. Cl. ..................... 502/20; 585/723; 585/730
[58] Field of Search ..................... 585/723, 730; 502/20

[56] References Cited

U.S. PATENT DOCUMENTS

| | | | |
|---|---|---|---|
| 2,551,881 | 5/1951 | Hachmuth | 202/40 |
| 2,914,590 | 11/1959 | Van Pool | 260/683.41 |
| 3,721,720 | 3/1973 | Chapman et al. | 260/683.48 |
| 3,793,394 | 2/1974 | Chapman | 260/683.48 |
| 3,975,164 | 8/1976 | Brown, Jr. | 585/723 |
| 4,199,409 | 4/1980 | Skraba | 203/39 |
| 4,454,369 | 6/1984 | Hutson, Jr. et al. | 585/719 |
| 4,663,026 | 5/1987 | Louie et al. | 208/262 |

FOREIGN PATENT DOCUMENTS

| | | |
|---|---|---|
| A-0184375 | 11/1986 | European Pat. Off. . |
| A-2123414 | 1/1972 | France . |

OTHER PUBLICATIONS

Perry et al. "Chemical Engineers' Handbook", Fifth Edition, 1973, pp. 18-3 to 18-5.

*Primary Examiner*—Asok Pal
*Attorney, Agent, or Firm*—Charles W. Stewart

[57] ABSTRACT

An improved process for the regeneration of an ASO-containing HF catalyst by the removal of ASO from said catalyst through the utilization of a separation column equipped with fixed valve fractionation trays. The separation column defines a separation zone having a top zone, an intermediate zone, and a bottom zone wherein contained within the bottom zone is a series of vertically spaced, fixed valve fractionation trays, wherein each of the fixed valve fractionation trays include a plate defining a plurality of apertures and wherein fixedly spaced above each of the apertures is a valve having a shape substantially the same as the apertures for directing the flow of gas passing upwardly through the apertures of the plate into the direction substantially parallel to the plate. One important aspect of the invention includes the use of the fixed valve fractionation trays in combination with the recycling of the bottoms stream in order to minimize the amount of hydrogen fluoride that passes with the ASO of the bottoms stream of the separation column.

5 Claims, 2 Drawing Sheets

REGENERATION OF HYDROGEN FLUORIDE ALKYLATION CATALYST

BACKGROUND OF THE INVENTION

This invention relates to the regeneration of a hydrogen fluoride catalyst used in an olefin and isoparaffin alkylation process.

In the process for alkylating olefins with isoparaffins in the presence of a hydrogen fluoride (HF) catalyst, a by-product called acid soluble oil (ASO) is produced. This ASO is soluble in the acid phase of an HF catalyst and, because of this solubility, over time, it will build-up in the acid phase of the HF catalyst. If not removed, a high ASO concentration will render the HF catalyst ineffective as an alkylation catalyst.

There are certain known methods for regenerating an HF alkylation catalyst, which contains a concentration of ASO, by removing the ASO therefrom. However, many of the known methods for regenerating an HF alkylation catalyst also result in a loss of HF that is lost along with the removed ASO.

SUMMARY OF THE INVENTION

It is thus an object of this invention to provide a process for regenerating an HF alkylation catalyst containing therein a concentration of ASO.

Another object of this invention is to provide an HF alkylation catalyst regeneration process which removes ASO from such HF alkylation catalyst with a minimum of loss of HF which is removed along with the ASO product.

Therefore, the inventive process provides for the regeneration of an HF catalyst used in the alkylation of olefins with isoparaffins and containing therein HF and ASO. Separation means for separating ASO from the HF catalyst is utilized. The separation means comprises a separation column, which defines a separation zone with the separation zone having a top zone, an intermediate zone, and a bottom zone, wherein contained within the bottom zone is a series of vertically spaced, fixed valve fractionation trays, wherein each of the fixed valve fractionation trays include a plate defining a plurality of appertures and wherein fixedly spaced above each of the appertures is a valve having a shape substantially the same as the appertures for directing the flow of gas passing upwardly through the appertures of the plate into the direction substantially parallel to the plate. HF catalyst is introduced into the intermediate zone of the separation column while a reflux of liquid isoparaffin is introduced into the top zone of the separation column and a vaporous isoparaffin stripping fluid is introduced into the bottom zone of the separation column but below the series of vertically spaced, fixed valve fractionator trays. Removed from the separation column is an overhead stream of HF and a bottom stream of ASO.

Other objects and advantages of the invention will be apparent from the detailed description of the invention and the appended claims.

DETAILED DESCRIPTION OF THE INVENTION

Figure 1:
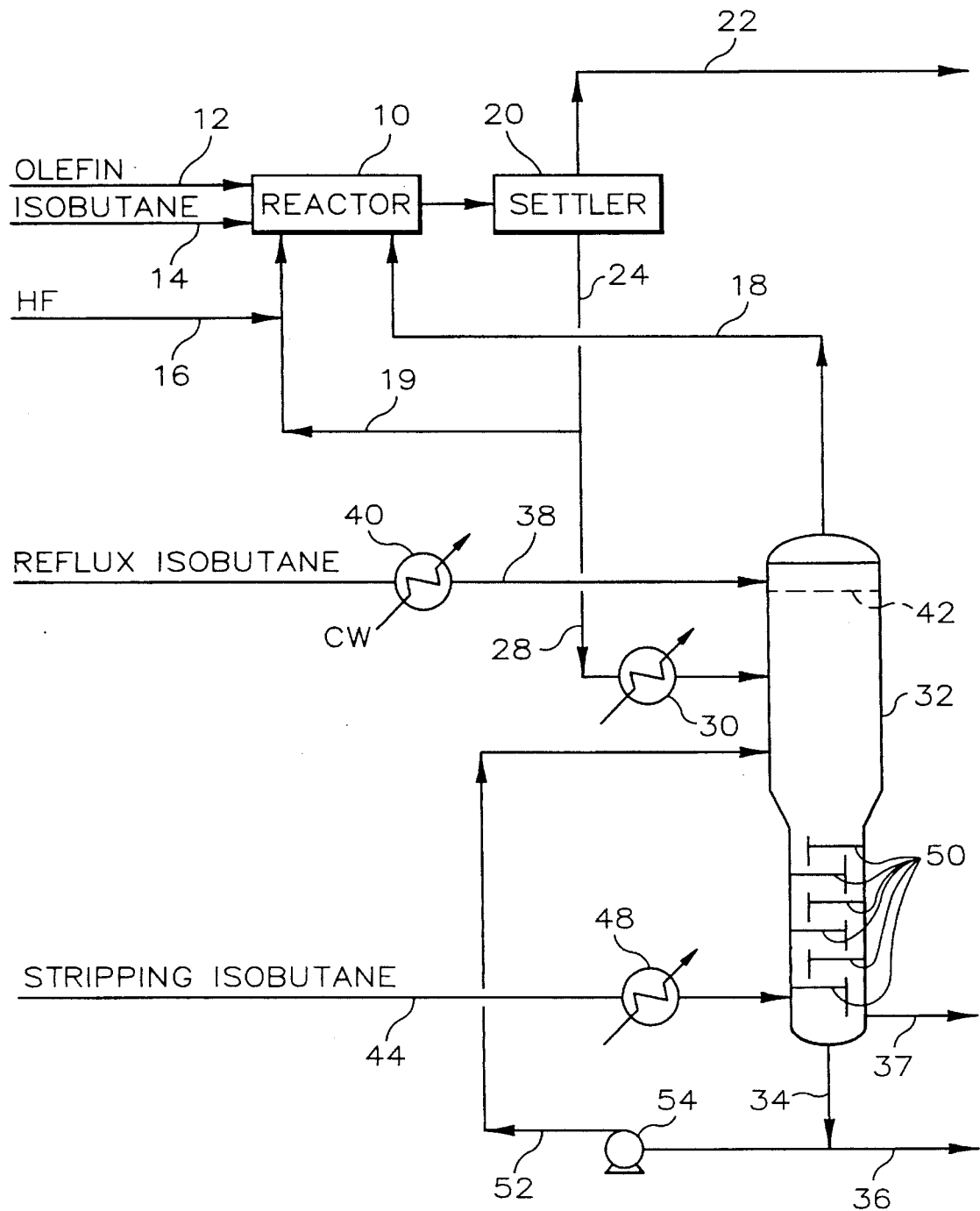
FIG. 1 is a schematic representation of the process which is one embodiment of the invention.

Referring now to FIG. 1 there is shown alkylation reactor 10 which defines an alkylation reaction zone. An olefin feed stream is introduced into alkylation reactor 10 through conduit 12 and an isoparaffin feed stream is introduced into alkylation reactor 10 through conduit 14. The olefin feed generally comprises one or more olefins having from 2 to 5 carbon atoms, while the isoparaffin stream generally comprises isobutane and/or isopentane. In a typical operation, the olefin feed comprises a mixture of propylene and butylenes, while the isoparaffin feed comprises primarily isobutane. A catalyst comprising hydrogen fluoride is introduced into alkylation reactor 10 through a conduit 16 and through recycle conduits 18 and 19. In a typical alkylation process operation, the HF is in the liquid phase and has a purity of at least about 90%. Fresh makeup catalyst can be introduced as required through a conduit 16. The effluent from alkylation reactor 10 is passed to a settler 20 in which a phase separation is made between the acid phase and hydrocarbon phase. The hydrocarbon phase is removed from settler 20 through conduit 22 and passes to downstream processing.

The acid phase is removed from settler 20 through conduit 24. At least a portion of the acid phase stream is recycled directly to alkylation reactor 10 through recycle conduit 19. The remainder of the acid phase stream is passed through conduit 28, having interposed therein heater 30 defining a heat transfer zone and providing means for transferring heat to the acid phase stream, to separator column 32. Separator column 32 defines a separation zone comprising a top zone, an intermediate zone, and a bottom zone and provides separation means for separating ASO from the HF of the acid phase. A purified HF stream is removed as an overhead stream from separator column 32 through conduit 18 and is recycled to alkylation reactor 10. An ASO stream can be removed as a bottoms stream from separator column 32 through conduits 34 and 36.

A liquid hydrocarbon reflux is introduced into the top zone of separator column 32 through conduit 38 having interposed therein condenser 40 defining a heat transfer zone and providing means for transferring heat to the liquid hydrocarbon reflux. The reflux is introduced onto distribution tray 42 located within the top zone of separator column 32. The bottom zone of separator column 32 is provided with a plurality of vapor-liquid contacting means, such as fixed valve fractionator trays 50. Stripping isobutane is directed to the bottom zone of separator column 32 by conduit 44. Interposed in conduit 44 is vaporizer 48 which defines a heat transfer zone and provides means for heating and/or vaporizing the stripping isobutane introduced into separator column 32.

A bottoms stream comprising ASO is removed from separator column 32 through conduit 34 and passes downstream by way of conduit 36. As an additional embodiment of the invention, at least a portion of the bottoms stream can be recycled or returned to separator column 32 by way of conduit 52. Interposed in conduit 52 is pump 54 for providing work input required to recycle the at least a portion of the bottoms stream to separator column 32. The at least a portion of the bottoms stream is introduced into the intermediate zone of separator column 32 at a location below the introduction entry point of the acid phase but above the bottom zone of separator column 32 wherein contained is a series of vertically spaced, fixed valve fractionator trays 50.

Figure 2:
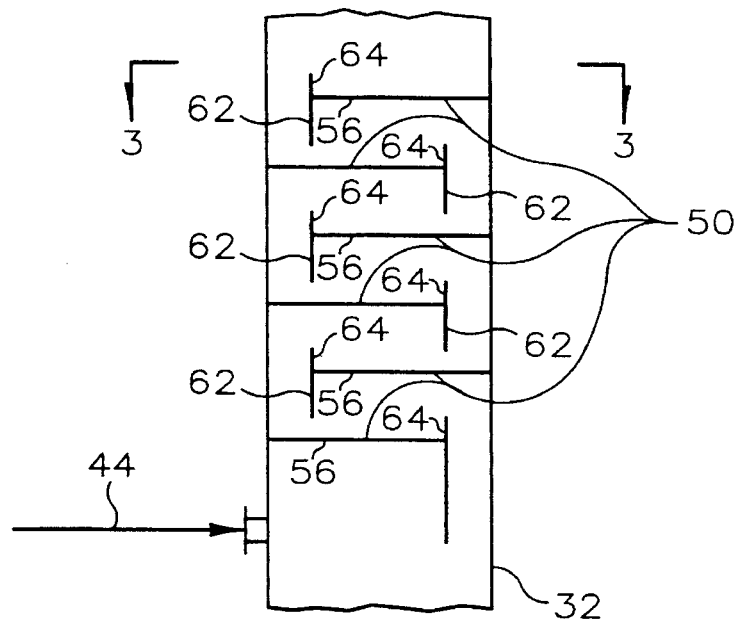
FIG. 2 is a vertical cross-sectional view of the tray section contained in the bottom zone of the separation column.
Figure 3:
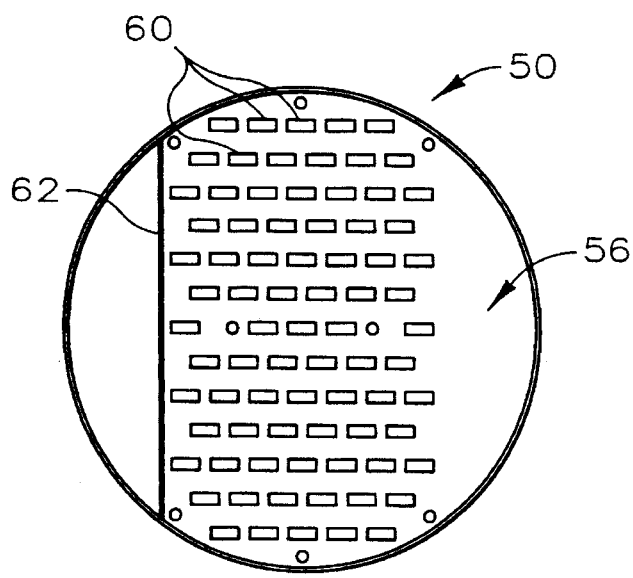
FIG. 3 is a horizontal cross-sectional view of the bottom zone of the separation column as viewed along section 3—3 and showing a fixed valve fractionator tray.

FIG. 2 provides an enlarged detail of the bottom zone of separator column 32 containing the series of vertically spaced, fixed valve fractionator trays 50. Each of the vertically spaced, fixed valve fractionator trays 50 include a plate or a deck 56 having a thickness and defining therein a pattern or plurality of appertures 60 (shown in FIG. 3) for permitting the upwardly flow of gas therethrough. Each individual apperture 60 defined by each plate 56 represents a cross-sectional area in the range of from about 0.005 square feet to about 0.40 square feet, preferably from about 0.01 square feet to about 0.30 square feet and, most preferably, from 0.015 square feet to 0.25 square feet.

Provided with each fixed valve fractionator tray 50 is a downcomer 62. Each downcomer 62 can comprise vertical plates secured along opposite edges thereof to the interior surface of separator column 32 so as to extend entirely across the interior of separator column 32. The vertical plate of downcomer 62 extends upwardly above the plane of plate 56 so as to provide an edge 64, which defines an overflow weir, having a height of from about 0.5 inches to about 4 inches, for retaining a level of liquid upon each plate 56. The vertical plate of downcomer 62 also extends downwardly to close proximity of the fixed valve fractionator tray 50 positioned below. The downcomers 62 are located on opposite sides of the interior of separator column 32 so as to guide liquids from a fixed valve fractionator tray 50 above to a fixed valve fractionator tray 50 below until the liquid passes along the last of such trays and is directed by its downcomer 62 to the bottom of separator column 32. Thus, the arrangement of fixed valve fractionator trays 50 and downcomers 62 provide for the stairstep type flow of liquids down the interior of separator column 32 with the liquid passing horizontally along each plate 56 and being directed to the tray below each downcomer 62.

The liquid is held on top of each tray by gases that flow upwardly through separator column 32 and passing through appertures 60. Preferably, the gas flow through appertures 60 should be sufficient to prevent a substantial portion of the liquid contained on top of each plate 56 to fall through such appertures and sufficient to maintain a level of liquid on top of each tray 50.

Figure 4:
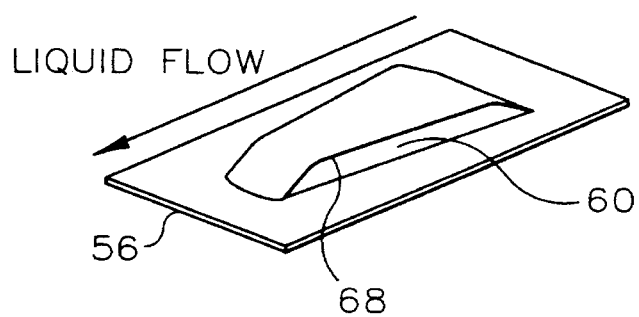
FIG. 4 is a perspective view of a single representative fixed valve of a fixed valve fractionator tray.

Provided in FIG. 4 is a close-up perspective view of a single apperture 60 and the associated fixed valve 68. As described earlier herein, each plate 56 shall define a plurality of appertures 60, but associated with each of such apperture 60 is a fixed valve 68 fixedly spaced above each apperture 60. The fixed valve 68 has substantially the same shape as its associated apperture 60 and is provided to direct the flow of the gases which are passing upwardly through appertures 60 in the horizontal direction parallel to plate 56. This configuration provides for the intimate contacting of the upwardly flowing gases with the liquid flowing across each plate 56. The distance of the fixed space above each apperture 60, as measured by the distance from the horizontal plane plate 56 and the horizontal plane of fixed valve 68, is in the range of from about 0.1 inches to about 0.5 inches, preferably from about 0.15 inches to about 0.45 inches and, most preferably, from 0.2 inches to 0.4 inches.

The key to the success of the process in the regeneration of an HF catalyst that contains a concentration of ASO is the use of separator column 32 that is properly equipped with fixed fractionator trays 50 as described herein. It has been found that the use of such trays in combination with the other features of the inventive process provide for a separation of ASO from the ASO-containing HF catalyst with a reduction in the amount of HF that is lost along with the ASO removed from the ASO-containing HF catalyst.

The ASO-containing HF catalyst is charged to the intermediate zone of separator column 32 at a temperature in the range of from about 200° F. to about 300° F., preferably, however, in the range of from 250° F. to 295° F. The temperature of the overhead stream of purified HF comprising HF can be in the range of from about 200° F. to about 300° F. and, preferably, between 250° F. and 295° F.

As for the isoparaffin reflux stream, its temperature can be in the range of from about 40° F. to about 140° F., preferably, 60° F. to 120° F. The preferred isoparaffin for use as the isoparaffin reflux stream is isobutane.

The stripping isoparaffin stream is introduced into the bottom zone of separator column 32 at an entry point below the series of vertically spaced, fixed valve fractionator trays contained within the bottom zone of separator column 32, and is in the form of a vapor or a gas. This vaporous isoparaffin rises upwardly through appertures 60 of each fixed valve fractionator tray 50 and provides for the separation of ASO and HF from the ASO-containing HF catalyst. The preferred stripping isoparaffin is isobutane, and it can have a temperature exceeding about 275° F. and, preferably, can be in the range of from 300° F. to 400° F.

The pressure at which column 32 is operated can generally be in the range of from 100 psia to 200 psia, preferably, from 125 psia to 175 psia.

The ASO-containing HF catalyst will generally have a concentration of ASO exceeding about 1.0 weight percent ASO based on the total weight of the ASO-containing HF catalyst. Specifically, the ASO concentration can be in the range of from about 1.25 weight percent to about 10 weight percent, and, more specifically, it can be in the range of from 1.5 weight percent to 5 weight percent.

The overhead stream of purified HF comprising HF shall have a concentration of ASO that is lower than that of the ASO-containing HF catalyst. Therefore, the ASO concentration will generally be less than 1.0 weight percent.

As for the bottoms stream of ASO, it is desirable to minimize the amount of ASO in such streams; and, indeed, this is an advantage of the instant invention in that the amount of ASO that is lost along with the ASO bottoms stream is much less than for other methods of regeneration of ASO-containing HF catalyst streams. The bottoms stream will comprise ASO at a concentration of at least about 50 weight percent based on the total weight of the bottoms streams. Preferably, the ASO concentration can be at least about 60 weight percent and, more preferably, it can be at least 70 weight percent.

It is most desirable to minimize the concentration of HF in the bottoms stream in order to also minimize the amount of HF lost with the bottoms stream, thus, the HF concentration can be less than about 50 weight percent of the bottoms stream, preferably less than about 40 weight percent and, most preferably less than 30 weight percent.

The following example is provided to further illustrate the invention and the benefits thereof.

EXAMPLE

The example summarizes the results of an actual installation and operation of the invention at the Phillips Petroleum Company refinery located at Sweeny, Tex. The process had experienced high acid losses with its use of a separation column containing therein conventional sloping or inclined trays. The inclined trays were removed from the separation column and replaced with fixed valve fractionator trays. After a period of operation, the data clearly establishes the enormously improved performance of the separation column and the significant reduction in the loss of HF with the ASO bottoms product.

The following Table I provides actual HF losses for each of six time periods immediately prior to the modification of the separation column and for each of seven time periods subsequent to the modification of the separation column. The data show that the average HF lost in the ASO bottoms product for the conventional process was 34,676 pounds per time period and was significantly higher than the average HF loss of 18,633 pounds per time period after the installation and operation of the novel process. These figures amounted to an average acid consumption in the associated alkylation process of 0.12 pounds HF per barrel alkylate produced for the conventional process versus 0.06 pounds of HF per barrel alkylate produced for the novel process.

TABLE I

| Time Period | LBS HF Lost With ASO Product | LBS Per Bbl Alkylate Produced |
| --- | --- | --- |
| Old Process | | |
| 1 | 42,420 | 0.15 |
| 2 | 50,500 | 0.16 |
| 3 | 26,260 | 0.09 |
| 4 | 30,300 | 0.12 |
| 5 | 26,260 | 0.08 |
| 6 | 32,320 | 0.10 |
| Average | 34,676 | 0.12 |
| New Process | | |
| 1 | 17,409 | 0.08 |
| 2 | 16,796 | 0.05 |
| 3 | 26,521 | 0.07 |
| 4 | 21,520 | 0.06 |
| 5 | 22,658 | 0.07 |
| 6 | 16,705 | 0.05 |
| 7 | 18,633 | 0.06 |
| | 18,633 | 0.06 |

While this invention has been described in terms of the presently preferred embodiment, reasonable variations and modifications are possible by those skilled in the art. Such variations and modifications are within the scope of the described invention and the appended claims.

That which is claimed is:

1. A process for regenerating an HF catalyst, containing HF and Acid Soluble Oil (hereinafter "ASO"), used in an olefin and isoparaffin alkylation process, comprising:

utilizing separation means for separating ASO from said HF catalyst, said separation means comprises a separator column which defines a separation zone and having a top zone, an intermediate zone, and a bottom zone, wherein contained within said bottom zone are a series of vertically spaced, fixed valve fractionation trays, wherein each of said fixed valve fractionation trays include a plate defining a plurality of appertures and wherein fixedly spaced above each of said appertures is a valve having a shape substantially the same as said appertures for directing the flow of gas passing upwardly through said appertures of said plate into the direction substantially parallel to said plate;

introducing said HF catalyst into said intermediate zone;

introducing, as a reflux, liquid isoparaffin into said top zone;

introducing into said bottom zone and below said series of vertically spaced, fixed valve fractionation trays a vaporous isoparaffin stripping fluid;

removing from said top zone an overhead stream of purified HF, comprising HF;

removing from said bottom zone a bottoms stream comprising ASO; and introducing at least a portion of said bottoms stream into said intermediate zone below the point of introduction of said HF catalyst.

2. A process as recited in claim 1 wherein each of said plurality of appertures defined by said plate represents a cross-sectional area in the range of from about 0.005 square feet to about 0.40 square feet.

3. A process as recited in claim 2 wherein the distance of the fixed space above each of said plurality of appertures as measured by the distance from the horizontal plane of said plate and the horizontal plane of said valve is in the range of from about 0.1 inches to about 0.5 inches.

4. A process as recited in claim 3 wherein the concentration of ASO in said HF catalyst exceeds about 1.0 weight percent based on the total weight of said HF catalyst and the concentration of ASO in said overhead stream of purified HF is less than 1.0 weight percent of said overhead stream.

5. A process as recited in claim 4 wherein the concentration of ASO in said bottoms stream is at least about 50 weight percent based on the total weight of said bottoms stream and the concentration of HF in said bottoms stream is less than about 50 weight percent of the total weight of said bottoms stream.

* * * * *